US006859666B1

(12) United States Patent
Clark et al.

(10) Patent No.: US 6,859,666 B1
(45) Date of Patent: Feb. 22, 2005

(54) COCHLEAR IMPLANT PACKAGE

(75) Inventors: Graeme Milbourne Clark, Eltham (AU); Brian Clive Pyman, Mont Albert (AU); Stephen O'Leary, Box Hill (AU)

(73) Assignee: University of Melbourne, Melbourne (AU)

( * ) Notice: Subject to any disclaimer, the term of this patent is extended or adjusted under 35 U.S.C. 154(b) by 153 days.

(21) Appl. No.: 10/018,988

(22) PCT Filed: Aug. 7, 2000

(86) PCT No.: PCT/AU00/00936

§ 371 (c)(1),
(2), (4) Date: Dec. 19, 2001

(87) PCT Pub. No.: WO01/10369

PCT Pub. Date: Feb. 15, 2001

(30) Foreign Application Priority Data

Aug. 6, 1999 (AU) .............................. PQ2071

(51) Int. Cl.⁷ ................................. A61N 1/05
(52) U.S. Cl. ....................................... 607/57
(58) Field of Search ........................ 607/55–57, 137; 623/10

(56) References Cited

U.S. PATENT DOCUMENTS 5,558,618 A    9/1996  Maniglia
5,814,095 A    9/1998  Muller et al.
5,906,635 A  * 5/1999  Maniglia ...................... 607/57
6,067,474 A  * 5/2000  Schulman et al. ............ 607/57

FOREIGN PATENT DOCUMENTS

| WO | WO 83/00999 A1 | 3/1983 |
| WO | WO 97/05673 A1 | 2/1997 |
| WO | WO 99/06108 A1 | 2/1999 |

OTHER PUBLICATIONS

PCT International Search Report dated Oct. 10, 2000; 3pp Listing (5) Cited References; for PCT/AU00/00936 (WO 01/10369 A1) filed Aug. 7, 2000 and published Feb. 15, 2001.

* cited by examiner

*Primary Examiner*—Kennedy Schaetzle
*Assistant Examiner*—Kristen Mullen
(74) *Attorney, Agent, or Firm*—Jagtiani+Guttag

(57) ABSTRACT

An implant package for a cochlear implant, including stimulator electronics contained within a protective housing (2) and being coupled to an electrode array (9) for insertion into the cochlea of a patient, and being further coupled to a receiving and/or transmitting coil (8) enclosed within a protective casing, said protective housing being dimensioned and shaped to be capable of location within the mastoid cavity (C) of the patient nearer to the entry point of the electrode array to the cochlea, said further coupling being contained in a flexible connection between the protective housing (2) and the protective casing (8).

10 Claims, 1 Drawing Sheet

US 6,859,666 B1

COCHLEAR IMPLANT PACKAGE

FIELD OF THE INVENTION

Figure 1:
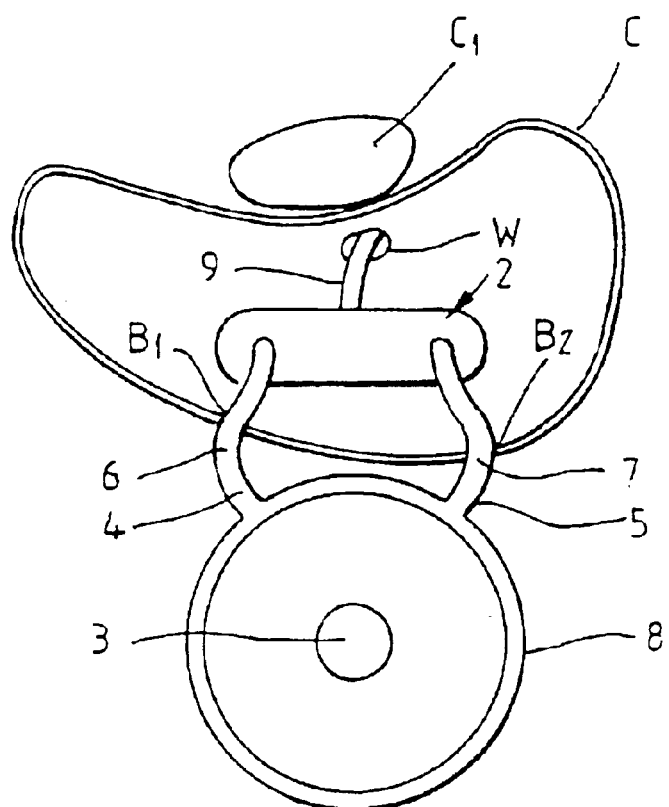

This invention relates to improvements in cochlear implants, and more particularly to improvements relating to the shapes of implant packages, e.g. receiver-stimulator packages, to enable the cochlear implant to be positioned in a patient in a more desirable location than the location presently used.

BACKGROUND OF THE INVENTION

Present cochlear implant receiver-stimulators are placed in a patient by drilling a bed into and through the posterior section of the mastoid bone lying behind the ear. The bed is usually made by drilling the bone down to the lining of the brain or dura mater. The receiver-stimulator of the Nucleus cochlear implant made by Cochlear Limited has a receiver-stimulator package made from titanium which houses the stimulation electronics and which is fitted into the bed in the mastoid bone. A receiver coil extends from the back end of the package and lies superficial to the bone. Other cochlear implants have included packages made from ceramic material and these are usually placed completely within a bed drilled down to the lining of the brain, especially in young children.

In young children, placing either of the above packages in the mastoid bone some distance behind the ear can lead to the packages creating an external swelling, which can be unsightly. More importantly, such placements of the package can lead to serious damage caused by excessive impact to the head in the area adjacent the implant. Such impact can lead to fractures of the electrode where it exits the package, or cracking or damage of the package itself. In addition, because the packages are placed in this particular location, especially where a bed is drilled down to the lining of the brain, it is possible for excessive impact to cause the package to enter the cranial cavity and damage structures including the brain.

SUMMARY OF THE INVENTION AND OBJECT

It is an object of the present invention to provide an improved implant package for a cochlear implant shaped to be received in a more desirable location within the skull of the patient.

The invention provides an implant package for a cochlear implant, said implant package including stimulator electronics contained within a protective housing and being operably coupled to an electrode array adapted for insertion into the cochlea of the patient, and being further operably coupled to a receiving and/or transmitting coil enclosed within a protective casing, said protective housing being dimensioned and shaped to be capable of location within the mastoid cavity of the patient nearer to the entry point of the electrode array to the cochlea, said further coupling being contained in a flexible connection between the protective housing and the protective casing.

By positioning the implant electronics housing in this way, the housing is less exposed to the risk of trauma caused by excessive blows to the head as it lies below the surface of the skull bone and is therefore less susceptible to a direct blow, and is additionally protected by the overlying pinna. The flexible coupling enables the coil to be placed in an optimal position and, depending on the anatomy and the age of the person, over time the coupling would adjust to any changes in head shape.

Advantageously, the implant package is electrically coupled to the electrode array and is further electrically coupled to the receiving and/or transmitting coil.

In a preferred form, the flexible coupling is made from a material having memory so that the coupling retains its desired shape when installed in the mastoid cavity. The flexible connection can include one or more flexible arms which contain the electrical leads for connecting the implant electronics in the protective housing to the transmitter/receiver coil. While two arms are shown in the preferred embodiment, one arm may have the advantage of reducing the inductive effects between the leads within the arms and the magnetic coil of the transmitter/receiver.

The implant package is preferably a receiver-stimulator package for a cochlear implant.

BRIEF DESCRIPTIONS OF THE INVENTION

A preferred embodiment of the invention will now be described with reference to the accompanying drawings in which:

FIG. 1 schematically illustrates one embodiment, and

Figure 2:
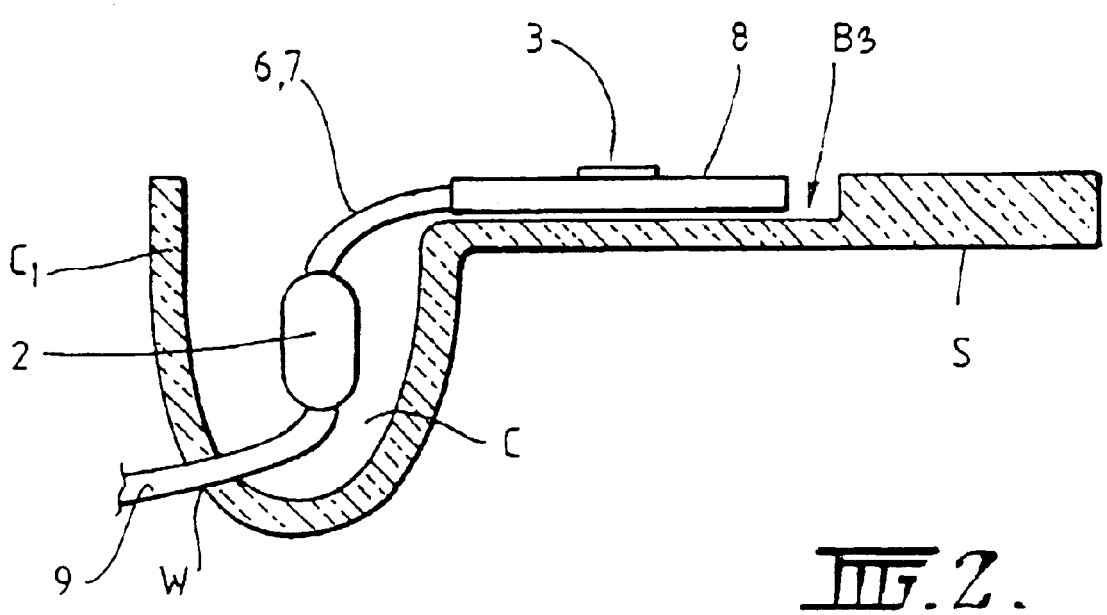

FIG. 2 is a schematic cross section illustrating the positioning of the protective casing and the protective housing relative to the ear canal, the mastoid cavity and the drilled bed in the skull.

DESCRIPTION OF THE PREFERRED EMBODIMENT

Anatomical dissections show that there is a gutter lying between the sigmoid sinus, posterior osseous ear canal, the mastoid tip and the floor of middle fossa where an appropriately shaped housing for the implant unit can be placed so that the housing is not exposed above the surface of the bone.

As illustrated in the drawings, the housing 2 comprises a narrow elongate rectangular housing having rounded ends, somewhat like a flattened ovoid or lozenge shape, which is received in the mastoid cavity C referred to above adjacent the ear canal $C_1$. The housing 2 may be made from titanium, similar to the Nucleus device, or from cast or moulded ceramic material.

As described above, the protective housing 2 for the implant electronics, in this case the receiver-stimulator electronics, is connected by suitable leads 4, 5 to a transmitter/receiver coil 3, the leads 4, 5 being contained within flexible arms 6, 7 of inert material such as silicone rubber. If desired, the arms 6, 7 can be formed from or incorporate a material having memory so that the arms retain their manufactured shape after installation.

The coil 3 is enclosed within a protective casing 8, which is received in a drilled bed $B_3$ in the mastoid bone behind the ear. Suitably shaped beds $B_1$, $B_2$ connecting the mastoid cavity and the drilled bed $B_3$ with the skull S receive the flexible arms 6, 7 containing the connecting leads 4, 5. A further lead 9 extends from the housing 2 into the ear canal $C_1$ through a window W and terminates in an electrode array (not shown) which is implanted in the cochlea.

Since the receiver-stimulator housing 2 is located in the mastoid cavity C, below the surface of the bone, it is less susceptible to damage and is protected and hidden by the overlying pinna. The flexible arm(s) 6, 7 allow optional positioning of the coil and permit changes in head shape.

The receiver-stimulator electronics, the transmitter/receiver coil, and the electrode array for implantation in the cochlea of the patient are configured in accordance with the patent literature relating to the cochlear implant technology and do not form any part of the present invention.

While one preferred shape for the protective housing has been described above, it will be appreciated that different shapes, which are capable of lying wholly within the gutter forming part of the mastoid cavity, can be adopted without departing from the essence of the invention defined above.

It is also envisaged that whilst the above embodiment is described with reference to a conventional cochlear implant system, i.e. one with a receiver-stimulator that receives coded signals from an external unit and provides stimulation to the cochlea accordingly, the present invention could equally be applied to a totally implanted cochlear implant system. In such a system the implant unit has the capability of functioning without the need for any external devices, at least for a defined period of time.

What is claimed is:

1. An implant package for a cochlear implant, said implant package including stimulator electronics contained within a protective housing and being operably coupled to an electrode array adapted for insertion into a cochlea of a patient, and being in electrical communication with a receiving and/or transmitting coil enclosed within a protective casing, said protective housing being dimensioned and shaped to be capable of location within a mastoid cavity of said patient, said electrical communication being contained in a flexible connection between said protective housing and said protective casing.

2. The implant package of claim 1, wherein said flexible connection facilitates optimal positioning of said receiving and/or transmitting coil, depending on anatomy and age of said patient.

3. The implant package of claim 1, wherein said flexible connection between said protective housing and said protective casing is such as to allow changes in head shape as said patient grows.

4. The implant package of claim 1, wherein the implant package is electrically coupled to the electrode array.

5. The implant package of claim 1, wherein the implant package is electrically coupled to the receiving and/or transmitting coil.

6. The implant package of claim 5, wherein the flexible connection includes one or more flexible arms containing leads which electrically connect the implant electronics to the receiving and/or transmitting coil.

7. The implant package of claim 1, wherein the implant package is a receiver-stimulator package for a cochlear implant.

8. The implant package of claim 1, wherein said flexible connection is made from a material having memory so that the coupling retains its shape after installation into the mastoid cavity.

9. An implant package for a cochlear implant, said implant package including stimulator electronics contained within a protective housing and being operably coupled to an electrode array adapted for insertion into a cochlea of a patient, and being further operably coupled to a receiving and/or transmitting coil enclosed within a protective casing, said protective housing being dimensioned and shaped to be capable of location within a mastoid cavity of said patient nearer to an entry point of said electrode array into said cochlea than said protective casing, said further coupling being contained in a flexible connection between said protective housing and said protective casing, wherein said flexible connection facilitates optimal positioning of said coil, depending on the anatomy and age of said patient, wherein said flexible connection between said protective housing and said protective casing is such as to allow changes in head shape as said patient grows, and wherein said flexible connection is made from a material having memory so that said further coupling retains its shape after installation into said mastoid cavity.

10. An implant package for a hearing implant, said implant package comprising:

a protective housing containing stimulator electronics;

at least one electrode adapted for insertion into an inner ear and in operable communication with said stimulator electronics;

a receiving and/or transmitting coil enclosed in a protective casing wherein said receiving and/or transmitting coil is electrically coupled to said protective housing; and a flexible connection between and directly attached to said protective housing and said protective casing, wherein said flexible connection includes one or more flexible arms contained leads which electrically connect the implant electronics to the receiving and/or transmitting coil.

* * * * *